US012605422B2

(12) United States Patent
Primor

(10) Patent No.: US 12,605,422 B2
(45) Date of Patent: Apr. 21, 2026

(54) COMPOSITIONS AND METHODS FOR TREATING DEGENERATIVE, AGE-RELATED AND TRAUMA-INDUCED DISORDERS

(71) Applicant: S.I.S SHULOV INNOVATIVE SCIENCE LTD., Rehovot (IL)

(72) Inventor: Naftali Primor, Jerusalem (IL)

(73) Assignee: S.I.S SHULOV INNOVATIVE SCIENCE LTD., Rehovot (IL)

( * ) Notice: Subject to any disclaimer, the term of this patent is extended or adjusted under 35 U.S.C. 154(b) by 1060 days.

(21) Appl. No.: 17/762,984

(22) PCT Filed: Sep. 23, 2020

(86) PCT No.: PCT/IL2020/051035
§ 371 (c)(1),
(2) Date: Mar. 23, 2022

(87) PCT Pub. No.: WO2021/059267
PCT Pub. Date: Apr. 1, 2021

(65) Prior Publication Data
US 2022/0362325 A1      Nov. 17, 2022

Related U.S. Application Data

(60) Provisional application No. 62/906,110, filed on Sep. 26, 2019.

(51) Int. Cl.
| | |
|---|---|
| *A61K 38/00* | (2006.01) |
| *A61K 9/00* | (2006.01) |
| *A61K 38/07* | (2006.01) |
| *A61P 25/28* | (2006.01) |
| *A61P 27/06* | (2006.01) |

(52) U.S. Cl.
CPC ............ *A61K 38/07* (2013.01); *A61K 9/0048* (2013.01); *A61P 25/28* (2018.01); *A61P 27/06* (2018.01)

(58) Field of Classification Search
CPC ........ A61K 38/07; A61P 25/28; C07K 5/1024
See application file for complete search history.

(56) References Cited

U.S. PATENT DOCUMENTS

| | | | |
|---|---|---|---|
| 4,619,916 A | 10/1986 | Di Stazio | |
| 6,815,425 B1 | 11/2004 | Meyerhoff | |
| 7,220,725 B2 | 5/2007 | Shulov | |
| 9,012,397 B2 | 4/2015 | Primor | |
| 2013/0310309 A1 * | 11/2013 | Primor | A61P 37/08 514/3.7 |

FOREIGN PATENT DOCUMENTS

| | | |
|---|---|---|
| CA | 3094295 A1 | 10/2019 |
| WO | 0128578 A2 | 4/2001 |
| WO | 0212269 A2 | 2/2002 |
| WO | 2012131676 A1 | 10/2012 |
| WO | 2019186561 A1 | 10/2019 |

OTHER PUBLICATIONS

Grace et al. Neurology; 2022;99:S1-S9.*
Byeon et al., (2010) Vascular endothelial growth factor as an autocrine survival factor for retinal pigment epithelial cells under oxidative stress via the VEGF-R2/PI3K/Akt. Invest Ophthalmol Vis Sci 51(2): 1190-1197.
Gaynes et al., (2013) Efficacy of a novel synthetic topical tetrapeptide on eliciting analgesia subsequent to experimentally induced chemical corneal injury. ARVO Annual Meeting Abstract. Investigative Ophthalmology & Visual Science 54(15): E-Abstract 5416.
Jarrett and Boulton (2012) Consequences of oxidative stress in age-related macular degeneration. Mol Aspects Med. Author manuscript; available in PMC Aug. 1, 2013. Published in final edited form as: Mol Aspects Med. Aug. 2012; 33(4): 399-417.
Jenner (1994) Oxidative damage in neurodegenerative disease. Lancet 344(8925): 796-798.
Lai et al., (2013) Ocular injury by transient formaldehyde exposure in a rabbit eye model. PLoS One 8(6): e66649.
Lin et al., (2017) Oroxylin A promotes retinal ganglion cell survival in a rat optic nerve crush model. PLoS One 12(6): e0178584.
Morrison et al., (2015) Modeling glaucoma in rats by sclerosing aqueous outflow pathways to elevate intraocular pressure. Exp Eye Res. Author manuscript; available in PMC Dec. 1, 2016. Published in final edited form as: Exp Eye Res. Dec. 2015; 141: 23-32.
Nakazawa et al., (2015) Hesperetin prevents selenite-induced cataract in rats. Mol Vis 21: 804-810.
Shearer et al., (1997) Selenite nuclear cataract: review of the model. Mol Vis 3: 8.

* cited by examiner

*Primary Examiner* — Jeanette M Lieb
(74) *Attorney, Agent, or Firm* — Allan A. Fanucci, Esq.

(57) ABSTRACT

Pharmaceutical compositions comprising specific tetrapeptides, for use in treating, preventing, minimizing, diminishing or reversing degenerative, age-related and trauma-induced disorders, particularly of the eye, are provided.

20 Claims, No Drawings
Specification includes a Sequence Listing.

COMPOSITIONS AND METHODS FOR TREATING DEGENERATIVE, AGE-RELATED AND TRAUMA-INDUCED DISORDERS

SEQUENCE LISTING

The Sequence Listing submitted herewith is an ASCII text file (2022-03-21_Sequence_Listing.txt, created on Mar. 21, 2022, 964 bytes), is filed via EFS-Web, and is hereby incorporated by reference.

FIELD OF THE INVENTION

The present invention relates to pharmaceutical compositions useful in treating, preventing, minimizing, diminishing or reversing degenerative, age-related and trauma-induced disorders, particularly of the eye.

BACKGROUND OF THE INVENTION

Degenerative disorders affect millions of people worldwide and are predominant in elderly population. The pathology of these diseases is typically attributed to the aberrant accumulation of protein aggregates resulting in from various pathogenic mechanisms including oxidative stress induced by Reactive Oxygen Species (ROS). Of the many degenerative disorders, eye-related degenerative disorders such as age-related macular degeneration (AMD) are a major public health concern that when left untreated can cause serious vision loss and blindness.

Age-related eye diseases and ocular injuries are typically considered irreversible. Current therapies are mainly directed at slowing down the progression of the disease and are often found to be inadequate. For example, currently approved drugs administered to glaucoma patients are designed to reduce the intra-ocular pressure. Their functionality stems from increasing the aqueous flow (parasympathomometics), decreasing of aqueous production (carbonic anhydrase inhibitors, $\alpha$ agonists), or increasing serum osmolarity to reduce intraocular water content (hyperosmotic agents). These drugs are not effective in treating old-age deterioration of retinal function since they do not interfere with the cell death cycle itself. Therapies for other diseases such as AMD also suffer from limited efficacy and/or significant adverse effects.

U.S. Pat. No. 4,619,916 describes thirteen tripeptides made from L-amino acids corresponding to the formula p-GLU-X-TRP where X is a specific amino acid different from p-GLU and Trp, as well as a process for their preparation, pharmaceutical formulations containing them and use thereof as hypotensive and analgesic agents.

U.S. Pat. No. 7,220,725 and WO 2002/012269 describe novel peptides including pGlu-Asn-Trp-Lys(Octanoyl)-OH (ZEP3) and pGlu-Asn-Trp-Thr-OH (ZEP4) and pharmaceutical compositions comprising an analgesic effective amount of a peptide for topical administration in the treatment of pain.

U.S. Pat. No. 9,012,397 and WO 2012/131676 describe topical pharmaceutical compositions including the peptides ZEP3 or ZEP4 and use thereof for treating a skin disorder selected from the group consisting of Herpes viral infection, Varicella viral infection, rash, insect bites, jellyfish stings, burns, psoriasis, itching, skin allergic response, skin lesions as a result of drug or medical treatment side effects or complications, and hypopigmentation.

Gaynes et al. (Invest. Ophthalmol. Vis. Sci. 54, E-Abstract 5416, 2013) describe an analgesic effect of the peptide ZEP4 in reducing ocular pain and modifying pathways of nociception in a rat model of experimentally induced chemical corneal injury.

WO 2019/186561 describes pharmaceutical compositions comprising specific tetrapeptides for use in reducing the release or inhibiting the activity of inflammatory cytokines and mediators. The application further relates to the treatment and amelioration of symptoms associated with the release of inflammatory cytokines in inflammatory conditions including inflammatory eye disorders.

There remains a yet unmet need for compositions and methods useful in treating degenerative, age-related, and trauma-induced disorders, particularly of the eye.

SUMMARY OF THE INVENTION

The present invention provides pharmaceutical compositions useful for treating, preventing, minimizing, diminishing or reversing a degenerative, age-related or trauma-induced disease or disorder, particularly of the eye.

The present invention is based, in part, on the unexpected finding that peptides denoted ZEP3 and ZEP4 and salts thereof attenuate the formation of reactive oxygen species (ROS) and increase viability of human primary corneal epithelial cells under stress conditions.

According to one aspect of the present invention, there is provided a pharmaceutical composition comprising as an active ingredient a peptide of Formula I: pGlu-$X_1$-$X_2$-$X_3$-OH, wherein $X_1$ is a polar amino acid residue; $X_2$ is an aromatic or hydrophobic amino acid residue; and $X_3$ is a positively charged or a polar amino acid residue, or a salt or derivative thereof; and a pharmaceutically acceptable excipient, for use in treating, preventing, minimizing, diminishing or reversing a degenerative, age-related or trauma-induced disease or disorder.

According to another aspect of the present invention, there is provided a method of treating, preventing, minimizing, diminishing or reversing a degenerative, age-related or trauma-induced disease or disorder in a subject in need thereof, the method comprising administering to the subject a pharmaceutical composition comprising as an active ingredient a peptide of Formula I: pGlu-$X_1$-$X_2$-$X_3$-OH, wherein $X_1$ is a polar amino acid residue; $X_2$ is an aromatic or hydrophobic amino acid residue; and $X_3$ is a positively charged or a polar amino acid residue, or a salt or derivative thereof; and a pharmaceutically acceptable excipient.

According to yet another aspect of the present invention, there is provided the use of a peptide of Formula I: pGlu-$X_1$-$X_2$-$X_3$-OH, wherein $X_1$ is a polar amino acid residue; $X_2$ is an aromatic or hydrophobic amino acid residue; and $X_3$ is a positively charged or a polar amino acid residue, or a salt or derivative thereof; and a pharmaceutically acceptable excipient for the preparation of a medicament for treating, preventing, minimizing, diminishing or reversing a degenerative, age-related or trauma-induced disease or disorder in a subject in need thereof.

According to an additional aspect of the present invention, there is provided a pharmaceutical composition comprising as an active ingredient a peptide of Formula I: pGlu-$X_1$-$X_2$-$X_3$-OH, wherein $X_1$ is a polar amino acid residue; $X_2$ is an aromatic or hydrophobic amino acid residue; and $X_3$ is a positively charged or a polar amino acid residue, or a salt or derivative thereof; and a pharmaceutically acceptable excipient, for use in treating, preventing, minimizing, diminishing or reversing a disease associated with ROS-related oxidative stress.

According to a further aspect of the present invention, there is provided a method of treating, preventing, minimizing, diminishing or reversing a disease associated with ROS-related oxidative stress in a subject in need thereof, the method comprising administering to the subject a pharmaceutical composition comprising as an active ingredient a peptide of Formula I: pGlu-$X_1$-$X_2$-$X_3$-OH, wherein $X_1$ is a polar amino acid residue; $X_2$ is an aromatic or hydrophobic amino acid residue; and $X_3$ is a positively charged or a polar amino acid residue, or a salt or derivative thereof; and a pharmaceutically acceptable excipient.

According to yet another aspect of the present invention, there is provided the use of a peptide of Formula I: pGlu-$X_1$-$X_2$-$X_3$-OH, wherein $X_1$ is a polar amino acid residue; $X_2$ is an aromatic or hydrophobic amino acid residue; and $X_3$ is a positively charged or a polar amino acid residue, or a salt or derivative thereof; and a pharmaceutically acceptable excipient for the preparation of a medicament for treating, preventing, minimizing, diminishing or reversing a disease associated with ROS-related oxidative stress in a subject in need thereof.

According to certain embodiments, the degenerative, age-related or trauma-induced disease or disorder comprises a degenerative, age-related or trauma-induced eye disease or disorder. According to particular embodiments, the degenerative, age-related, or trauma-induced eye disease or disorder is selected from the group consisting of glaucoma, fuchs' corneal dystrophy, cataract or trauma induced following cataract surgery, corneal erosion, and age-related macular degeneration. Each possibility represents a separate embodiment.

According to some embodiments, the degenerative disease or disorder is a neurodegenerative disease or disorder selected from the group consisting of Alzheimer's disease, Parkinson's disease, Huntington's disease, and Amyotrophic Lateral Sclerosis (ALS). Each possibility represents a separate embodiment.

According to additional embodiments, the disease associated with ROS-related oxidative stress is atherosclerosis. According to other embodiments, the disease associated with ROS-related oxidative stress is chronic obstructive pulmonary disease (COPD).

According to some embodiments, $X_1$ is selected from the group consisting of Asn, Gln, His, Ser, Thr, Tyr, and Cys; $X_2$ is selected from the group consisting of Trp, Phe, Tyr, Ala, Ile, Leu, Met, Val, and Gly; and $X_3$ is selected from the group consisting of Lys, Lys derivative, Arg, His, Asn, Gln, Ser, Thr, and Tyr. Each possibility represents a separate embodiment.

According to other embodiments, $X_1$ is selected from the group consisting of Asn and Thr; $X_2$ is selected from the group consisting of Trp, Phe and Tyr; and $X_3$ is selected from the group consisting of Lys, Lys derivative, and Thr. Each possibility represents a separate embodiment.

According to various embodiments, the peptide derivative comprises a peptide of Formula I having an alkyl group attached to a free functional group of the peptide sequence.

According to yet other embodiments, the alkyl group is attached by an amide bond or linkage to a free amino group of a side chain or the N-terminus of the peptide.

According to some embodiments, the alkyl is a $C_4$-$C_{30}$ alkyl.

According to specific embodiments, a $C_8$ alkyl (herein octanoyl), is attached by an amide linkage to a terminal amino group of the peptide or the side chain of a Lys residue of the peptide sequence. In accordance with the latter embodiments, the Lys derivative is Lys(Octanoyl).

According to some embodiments, the C-terminus of the peptide is modified, to form an amide, alcohol or ester terminus. Each possibility represents a separate embodiment.

According to certain embodiments, the peptide of Formula I or a salt or derivative thereof is selected from the group consisting of pGlu-Asn-Trp-Lys(Octanoyl)-OH (SEQ ID NO: 1), pGlu-Asn-Trp-Thr-OH (SEQ ID NO: 2), and salts thereof. Each possibility represents a separate embodiment.

According to some embodiments, the peptide of Formula I or a salt or derivative thereof has an amino acid sequence as set forth in SEQ ID NO: 1 or a salt thereof.

According to other embodiments, the peptide of Formula I or a salt or derivative thereof has an amino acid sequence as set forth in SEQ ID NO: 2 or a salt thereof.

According to various embodiments, the pharmaceutical composition comprises a sodium salt of a peptide or peptide derivative of Formula I having a sequence as set forth in any one of SEQ ID NO: 1 and SEQ ID NO: 2. Each possibility represents a separate embodiment.

According to certain embodiments, the pharmaceutical composition comprises from about 0.1% to about 5% w/w of the peptide of Formula I or a salt or derivative thereof including each value within the specified range. According to particular embodiments, the pharmaceutical composition comprises from about 0.5% to about 2% w/w of the peptide of Formula I or a salt or derivative thereof including each value within the specified range.

In some embodiments, the pharmaceutical composition is formulated for administration via a route selected from the group consisting of topical (e.g. ocular), oral, transdermal, intra-arterial, intranasal, intraperitoneal, intramuscular, subcutaneous, and intravenous. Each possibility represents a separate embodiment.

In other embodiments, the pharmaceutical composition is in a form selected from the group consisting of solution, suspension, dispersion, emulsion, oil, ointment, gel, cream, lotion, tablet, pill, capsule (e.g. soft or hard gelatin capsule), pellets, granules, powder, a wafer, coated or uncoated beads, lozenge, sachet, cachet, elixir, an osmotic pump, a depot system, an iontophoretic system, a patch, syrup, aerosol, and suppository. Each possibility represents a separate embodiment. In embodiments pertaining to ocular administration, the pharmaceutical composition is preferably in a form selected from the group consisting of solution, suspension, dispersion, emulsion, oil, ointment, gel, cream, and lotion. Each possibility represents a separate embodiment.

In particular embodiments, the pharmaceutically acceptable excipient comprises at least one of a binder, a filler, a diluent, a surfactant or emulsifier, a glidant or lubricant, a buffering or pH adjusting agent, a tonicity enhancing agent, a wetting agent, a thickening agent, a suspending agent, a preservative, an antioxidant, a solvent, a flavoring agent, a colorant, and a mixture or combination thereof. Each possibility represents a separate embodiment. In embodiments pertaining to ocular administration, the pharmaceutically acceptable excipient is preferably at least one of an osmotic agent, a chelating agent, a buffering or a pH adjusting agent, a preservative, an antioxidant, a filler, a surfactant, a wetting agent, a thickening agent, a suspending agent, a tonicity enhancing agent, a solvent, and a mixture or combination thereof. Each possibility represents a separate embodiment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

The present invention relates to pharmaceutical compositions comprising specific peptides and salts or derivatives thereof, useful in preventing, minimizing, diminishing or reversing degenerative, age-related and trauma-induced disorders, particularly of the eye. The present invention further relates to pharmaceutical compositions comprising said peptides and salts or derivatives thereof, useful in treating, preventing, minimizing, diminishing or reversing a disease associated with ROS-related oxidative stress.

The principles and operation of the present invention may be better understood with reference to the accompanying descriptions. Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is based, in part, on the surprising discovery that the peptides ZEP3 and ZEP4, and their sodium salt forms, reduced the formation of reactive oxygen species (ROS) and increased viability of human primary corneal epithelial cells under stress conditions (70 mM NaCl). Reactive oxygen species (ROS) can cause major damage to cells by oxidizing lipids, proteins, carbohydrates and DNA in cells and tissues. This undesirable oxidation results in membrane damage, protein modification, and DNA impairment that can give rise to death of cells and tissues. Reducing the formation of ROS and increasing viability of human primary corneal epithelial cells under stress conditions using the peptides of the present invention indicate that the peptides claimed herein provide beneficial therapeutic effect in treating, preventing, minimizing, diminishing or reversing degenerative and age-related disorders or in treating, preventing, minimizing, diminishing or reversing disorders induced by trauma, particularly to the eye.

According to certain aspects and embodiments, there is provided a pharmaceutical composition comprising as an active ingredient a peptide of Formula I or a salt or derivative thereof and a pharmaceutically acceptable excipient, for use in treating, preventing, minimizing, diminishing or reversing a disease associated with ROS-related oxidative stress. According to other aspects and embodiments, there is provided a method of treating, preventing, minimizing, diminishing or reversing a disease associated with ROS-related oxidative stress in a subject in need thereof, the method comprising administering to the subject a pharmaceutical composition comprising as an active ingredient a peptide of Formula I or a salt or derivative thereof; and a pharmaceutically acceptable excipient. Use of a peptide of Formula I or a salt or derivative thereof; and a pharmaceutically acceptable excipient for the preparation of a medicament for treating, preventing, minimizing, diminishing or reversing a disease associated with ROS-related oxidative stress in a subject in need thereof is provided as well.

According to further aspects and embodiments, the pharmaceutical composition comprising as an active ingredient a peptide of Formula I or a salt or derivative thereof and a pharmaceutically acceptable excipient is useful in treating, preventing, minimizing, diminishing or reversing a degenerative, age-related, or trauma-induced disease or disorder, particularly a degenerative, age related, or trauma-induced eye disease or disorder. According to additional aspects and embodiments, there is provided a method of treating, preventing, minimizing, diminishing or reversing a degenerative, age-related, or trauma-induced disease or disorder, particularly a degenerative, age-related, or trauma-induced eye disease or disorder, the method comprising administering to a subject in need thereof a pharmaceutical composition comprising as an active ingredient a peptide of Formula I or a salt or derivative thereof; and a pharmaceutically acceptable excipient. Use of a peptide of Formula I or a salt or derivative thereof; and a pharmaceutically acceptable excipient for the preparation of a medicament for treating, preventing, minimizing, diminishing or reversing a degenerative, age-related, or trauma-induced disease or disorder, particularly a degenerative, age-related, or trauma-induced eye disease or disorder in a subject in need thereof is provided as well. According to the principles of the present invention, the peptides, peptide derivatives, and salts disclosed herein provide beneficial therapeutic effect in degenerative, age-related, or trauma-induced eye disorders, wherein the beneficial therapeutic effect does not include the treatment of pain or inflammation per se. Accordingly, treatment is affected in these disorders even in the absence of pain and/or inflammation.

According to various aspects and embodiments, the peptide of Formula I is represented by the following structure pGlu-$X_1$-$X_2$-$X_3$-OH, wherein pGlu is pyroglutamic acid; $X_1$ is a polar amino acid residue; $X_2$ is an aromatic or hydrophobic amino acid residue; and $X_3$ is a positively charged amino acid residue or a polar amino acid residue. It is to be understood that the —OH in Formula I indicates a native carboxy terminus.

As used herein, the term "a polar amino acid residue" refers to the following amino acids: Asparagine (Asn; N), Glutamine (Gln; Q), Histidine (His; H), Serine (Ser; S), Threonine (Thr; T), Tyrosine (Tyr; Y), and Cysteine (Cys; C). Each possibility represents a separate embodiment.

As used herein, the term "an aromatic amino acid residue" refers to the following amino acids: Tryptophan (Trp; W), and Tyrosine (Tyr; Y). Each possibility represents a separate embodiment.

As used herein, the term "a hydrophobic amino acid residue" refers to the following amino acids: Alanine (Ala; A), Isoleucine (Ile; I), Leucine (Leu; L), Methionine (Met; M), Phenylalanine (Phe; F), Valine (Val; V), and Glycine (Gly; G). Each possibility represents a separate embodiment.

As used herein, the term "a positively charged amino acid residue" refers to the following amino acids: Lysine (Lys; K) and a derivative thereof, Arginine (Arg; R), and Histidine (His; H). Each possibility represents a separate embodiment.

It is contemplated that the amino acid residues of the present invention include both D- and L-amino acids, preferably L-amino acids.

In further embodiments of the present invention, $X_1$ is selected from the group consisting of Asn and Thr. Each possibility represents a separate embodiment.

In other embodiments of the present invention, $X_2$ is selected from the group consisting of Trp, Phe, and Tyr. Each possibility represents a separate embodiment.

In yet other embodiments of the present invention, $X_3$ is selected from the group consisting of Lys, Lys derivative, and Thr. Each possibility represents a separate embodiment.

In further embodiments of the present invention, $X_1$ is selected from the group consisting of Asn and Thr; $X_2$ is selected from the group consisting of Trp, Phe, and Tyr; and $X_3$ is selected from the group consisting of Lys, Lys derivative, and Thr. Each possibility represents a separate embodiment.

Also included within the scope of the present invention are salts and derivatives of the peptides used in the disclosed compositions and methods.

As used herein, the term "salts" refers to salts of carboxyl groups also termed base addition salts and to acid addition salts of amino or guanidino groups of the peptide molecule. Suitable base addition salts include, but are not limited to, metallic salts of sodium, calcium, lithium, magnesium, potassium, aluminum, ferric and zinc; ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl)amine, phenylethylbenzylamine, dibenzylethylenediamine, procaine, chloroprocaine, piperidine, monoethanolamine, triethanolamine, quinine, choline, N-methylglucosamine. Each possibility represents a separate embodiment. Salts with amino acids such as glycine, ornithine, histidine, phenylglycine, lysine, and arginine are contemplated. Each possibility represents a separate embodiment. Furthermore, any zwitterionic salts formed by a carboxylic acid and an amino or guanidino groups of the peptide molecule are contemplated as well.

Suitable acid addition salts include salts derived from inorganic acids such as, but not limited to, hydrochloric, nitric, phosphoric, sulfuric, hydrobromic, hydriodic, phosphorous, and the like, as well as salts derived from organic acids such as aliphatic mono- and dicarboxylic acids such as acetic acid or oxalic acid, phenyl-substituted alkanoic acids, hydroxy alkanoic acids, alkanedioic acids, aromatic acids, aliphatic and aromatic sulfonic acids and the like. Each possibility represents a separate embodiment. The salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Each possibility represents a separate embodiment. Also contemplated are salts of amino acids such as arginate and the like and gluconate or galacturonate. Each possibility represents a separate embodiment.

The acid addition salts may be prepared by known methods of the art in which the free base form is brought into contact with a sufficient amount of the desired acid to produce the salt. The base addition salts may be prepared by known methods of the art in which the free acid form is brought into contact with a sufficient amount of the desired base to produce the salt.

"Derivatives" of the peptides of the invention as used herein cover derivatives which may be prepared from the functional groups which occur as side chains on the residues or the N- or C-terminal groups, by means known in the art, and are included in the invention provided that they do not adversely affect the therapeutic benefits of the peptide and do not confer toxic properties to compositions containing it.

These derivatives may include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or aroyl groups), or O-acyl derivatives of free hydroxyl group (e.g., that of seryl or threonyl residues) formed by reaction with acyl moieties.

In particular embodiments of the present invention, the peptide derivative comprises an alkyl group attached to a free functional group of the peptide sequence.

In certain embodiments, the alkyl group is attached by an amide bond or linkage to a free amino group of a side chain or the N-terminus of the peptide. The alkyl group may be a $C_4$-$C_{30}$ alkyl, preferably a $C_8$ alkyl (herein octanoyl) which is attached by an amide linkage to the side chain of a Lys residue of the peptide sequence (Lys(Octanoyl)) or a terminal amino group of the peptide. The skilled in the art can appreciate that lysine has an amino-containing side chain. As such, peptides encompassing lysine may be modified through said lysine side chain amino functionality. Specifically, the lysine side chain amino group is a primary amine ($-NH_2$), which is convertible to an amide by its reaction with a carboxylic acid containing moiety. It is to be understood that the term "Lys(Octanoyl)" refers to the product of such a reaction, wherein the lysine amino side chain is reacted with octanoic acid thereby forming an octanoyl amide ($C_7H_{15}C(O)NH$) comprising an octanoyl group ($C_7H_{15}C(O)$). It is further to be understood that when referring to "alkyl" in the context of the chemical substitution of the lysine's amino side chain, the reference is to the group chemically bonded to the carbonyl. In other words, reference is made to a fragment having the chemical structure $RC(O)NH$, wherein R is an alkyl group, e.g. R is $C_7H_{15}$.

According to some embodiments, the C-terminus of the peptide is modified, to form an amide, alcohol or ester terminus. Each possibility represents a separate embodiment.

The peptides, derivatives and salts used in the compositions and methods of the present invention may be synthesized using any method known in the art including, but not limited to, solid phase and liquid phase peptide synthesis. Some of the peptides used in the compositions of the present invention may be produced using recombinant methods or combination of recombinant and synthetic methods.

In exemplary embodiments of the present invention, the peptide derivative is pGlu-Asn-Trp-Lys(Octanoyl)-OH (SEQ ID NO: 1; hereinafter referred to as "ZEP3"), wherein pGlu is pyroglutamic acid. ZEP3 can be produced, for example, by the procedure described in U.S. Pat. No. 7,220,725.

In another exemplary embodiment of the present invention, the peptide derivative is pGlu-Asn-Trp-Thr-OH (SEQ ID NO: 2; hereinafter referred to as "ZEP4"). ZEP4 can be produced, for example, by the following procedure:

The synthesis of ZEP4 may be performed by a sequential synthesis of 9-fluoromethoxycarbonyl (Fmoc) amino acids on a solid support of chlorotrityl chloride resin (CTC). CTC resin (125 gr) is loaded with Fmoc-threonine (t-butyl; 79 gr) and diisopropyl ethylamine (DIPEA; 160 gr) is used as the coupling agent of the amino acid to the solid support. The Fmoc protecting group is removed by a mixture of 25% piperidine and dimethylformamide (DMF) and the resin-peptide is filtered and washed with DMF. A second amino acid, Fmoc-Trp (85 gr), is activated by a mixture of (2-(1H-benzotriazol-1-yl)-1,1,3,3-tetramethyluronium hexafluorophosphate (HBTU)/hydroxy benzothiazole (OHBT) coupled to the first amino acid by addition of DIPEA. The Fmoc group is removed as described hereinabove and the resin-peptide is filtered and washed with DMF. A third amino acid, Fmoc-Asn (trt) (119 gr) is activated by HBTU/HOBT and coupled by addition of DIPEA. The Fmoc group is removed as described hereinabove and the resin-peptide is filtered and washed with DMF. A fourth amino acid pGlu (26 gr) is activated by HBTU/HOBT and coupled by DIPEA.

The peptide-resin is thoroughly washed with DMF followed by IPA and dried under reduced pressure. The peptide is cleaved from the resin and protecting groups of the Thr and Asn as well by TFA (95%) and triisopropyl silane (TIS) (5%) at room temperature for 2 hours. The peptide is precipitated by addition of methyl tert-butyl ether (MTBE), filtered and dried (yield 46 gr).

The crude product (46 gr) is dissolved in a mixture of acetonitrile (ACN) and water and loaded on preparative HPLC system (4", RP C-18 100-120 A pore size) and purified using a gradient system containing Phase A—0.1% TFA in water; and Phase B—ACN. The elution is done by gradually increasing phase B (3% to 33%) during 45 minutes. Fractions having purity greater than 97% are collected. The combined fractions are eluted on the same HPLC system using a gradient containing Phase A: 0.2% acetic acid; and Phase B: ACN. The elution is performed by gradually increasing phase B (10% to 40%) during 30 minutes. Fractions having purity greater than 97% are collected, combined, and lyophilized (yield 29 gr). The final product has M.W. (MS) of 530.5; and 97.3% purity (HPLC).

In one embodiment of the present invention, the peptide is the sodium salt of the peptide derivative set forth in SEQ ID NO: 1 (pGlu-Asn-Trp-Lys(Octanoyl)-OH.nNa wherein n is 1 or 2; hereinafter referred to as "ZEP3 sodium salt" or "ZEP3Na"). In particular embodiments, the sodium salt of the peptide derivative comprises the following formula: pGlu-Asn-Trp-Lys(Octanoyl)-ONa. ZEP3 sodium salt can be produced, for example, by the following procedure:

ZEP3 (3.1 g) is solubilized in $NaHCO_3$ (100 mM) in water (50 g/l). The solution is injected into an HPLC ion exchange column (2.5×22 cm Luna C18, 100 A, 15 micron) and eluted by a gradient consisting of: Mobile Phase A: $NaHCO_3$ 2 mM in $H_2O$; Mobile Phase B: $NaHCO_3$ 2 mM in $CH_3CN/H_2O$ (8/2); and Mobile Phase C: $NaHCO_3$ 100 mM in water. Loading per run: 5% maximum (W/W % Peptide/Stationary Phase). Flow: 4.8 cm/min (24 ml/min). The gradient procedure is as follows: 20 min phase C; 5 min Phase A; 18 min Phase B; and 7 min Phase C. A fraction containing the product is collected and concentrated under reduced pressure to remove acetonitrile (110 g/l) then freeze dried [yield 2.2 g (71%)]. The final product has 99.7% purity (HPLC), 3.1% sodium content and solubility of 50 mg/ml water.

In another embodiment of the present invention, the peptide is the sodium salt of the peptide set forth in SEQ ID NO: 2 (pGlu-Asn-Trp-Thr-OH.nNa wherein n is 1 or 2; hereinafter referred to as "ZEP4 sodium salt" or "ZEP4Na"). In particular embodiments, the sodium salt of the peptide derivative comprises the following formula: pGlu-Asn-Trp-Thr-ONa. ZEP4 sodium salt can be produced, for example, by the following procedure:

ZEP4 (5 g) is solubilized in $NaHCO_3$ (100 mM) in water (50 g/l). The solution is injected into an HPLC ion exchange column (2.5×22 cm Luna C18, 100 A, 15 micron) and eluted by a gradient consisting of: Mobile Phase A: $NaHCO_3$ 2 mM in $H_2O$; Mobile Phase B: $NaHCO_3$ 2 mM in $CH_3CN/H_2O$ (8/2); and Mobile Phase C: $NaHCO_3$ 100 mM in water. Loading per run: 5% maximum (W/W % Peptide/Stationary Phase). Flow: 4.8 cm/min (24 ml/min). The gradient procedure is as follows: 20 min phase C, then 5 min Phase A, then 20 min Phase B, and 10 min Phase C. A fraction containing the product is collected and concentrated under reduced pressure to remove acetonitrile (110 g/l) then freeze dried [yield 4 g (80%)]. The final product has 97.5% purity (HPLC), 2.5% sodium content and solubility of 50 mg/ml water.

The peptides of the present invention can be used as pharmaceutical agents per se or as part (active ingredient) of a pharmaceutical composition together with a pharmaceutically acceptable excipient. In accordance with these embodiments, the composition may comprise from about 0.1% to about 5% w/w of the peptide, including each value within the specified range. According to other embodiments, the composition comprises from about 0.5% to about 2% w/w of the peptide, including each value within the specified range. According to yet other embodiments, the composition comprises about 1% of the peptide. In various embodiments, the amount of peptide ranges from about 200 µg to about 800 µg per gram composition, including each value within the specified range. In further embodiments, the amount of peptide ranges from about 300 µg to about 700 µg per gram composition, including each value within the specified range. In additional embodiments, the amount of peptide ranges from about 400 µg to about 600 µg per gram composition, including each value within the specified range. In particular embodiments, the amount of peptide is about 500 µg per gram composition.

As used herein a "pharmaceutical composition" refers to a preparation of the peptide of formula I with one or more chemical components such as pharmaceutically acceptable excipients designed to facilitate administration of a compound to a subject, preferably a human subject. The term "pharmaceutically acceptable excipient" as used herein refers to an excipient that does not abrogate the beneficial therapeutic activity and properties of the peptide of the present invention. Suitable pharmaceutically acceptable excipients within the scope of the present invention include, but are not limited to, a binder, a filler, a diluent, a surfactant or emulsifier, a glidant or lubricant, a buffering or pH adjusting agent, a tonicity enhancing agent, a wetting agent, a thickening agent, a suspending agent, a preservative, an antioxidant, a solvent, a flavoring agent, a colorant, and a mixture or combination thereof. Each possibility represents a separate embodiment.

Suitable binders include, but are not limited to, povidone (PVP: polyvinyl pyrrolidone), copovidone, hydroxypropyl cellulose (HPC), hydroxypropyl methylcellulose (HPMC), carboxy methyl cellulose (CMC), hydroxyethylcellulose, gelatin, polyethylene oxide, poly ethylene glycol (PEG), poly vinyl alcohol (PVA), acacia, chitin, chitosan, dextrin, magnesium aluminum silicate, starch, and polymethacrylates, or a mixture or combination thereof. Each possibility represents a separate embodiment. In one embodiment, the pharmaceutical composition comprises from about 0% to about 40% w/w of a binder, including each value within the specified range.

Suitable fillers include, but are not limited to, mica, talc, silicon dioxide, nylon, polyethylene, silica, polymethacrylate, kaolin, calcium carbonate, calcium phosphate, microcrystalline cellulose, various sugars and types of starch, polysugars, dextrin, cyclodextrins (e.g. β-CD, hydroxypropyl-β-CD, sulfobutylether-CD), and Teflon, or a mixture or combination thereof. Each possibility represents a separate embodiment. In one embodiment, the pharmaceutical composition comprises from about 0.5% to about 50% w/w of a filler, including each value within the specified range.

Suitable diluents include, but are not limited to, dicalcium phosphate dihydrate, sugars, lactose, trehalose, cyclodextrins, calcium phosphate, cellulose, kaolin, mannitol, sodium chloride, and dry starch, or a mixture or combination thereof. Each possibility represents a separate embodiment. In one embodiment, the pharmaceutical composition comprises from about 0.5% to about 50% w/w of a diluent, including each value within the specified range.

Suitable surfactants are cationic, anionic or zwitterionic including, but not limited to, polyoxyethylene glycol octylphenol ethers, polyoxyethylene glycol alkylphenol ethers, polyoxyethylene glycol sorbitan alkyl esters (polysorbate 60, polysorbate 80, etc.), polyethyleneglycol tocopheryl succinate, polyethoxylated castor oil derivatives (Cremophor El, Cremophor Rh40), tyloxapol, sorbitan alkyl esters, block copolymers of polyethylene glycol and polypropylene glycol (poloxamer), dioctyl sodium sulfosuccinate, perfluorooctanesulfonate, alkylbenzene sulfonates, sodium lauryl ether sulfate, ammonium laureth sulfate, ammonium lauryl sulfate, disodium laureth sulfosuccinate, lignosulfonate, sodium stearate, benzalkonium chloride, cetyl pyridinium chloride, benzethonium chloride, cetyl trimethylammonium bromide, cetyl trimethylammonium chloride, and betaines, or a mixture or combination thereof. Each possibility represents a separate embodiment. In one embodiment, the pharmaceutical composition comprises from about 0% to about 5% w/w of a surfactant, including each value within the specified range.

Suitable emulsifiers include, but are not limited to, polyethylene glycol ethers of stearic acid such as steareth-2, steareth-4, steareth-6, steareth-7, steareth-10, steareth-11, steareth-13, steareth-15, and steareth-20, glyceryl stearate, stearyl alcohol, cetyl alcohol, cetearyl alcohol, behenyl alcohol, diethanolamine, lecithin, and polyethylene glycols, or a mixture or combination thereof. Each possibility represents a separate embodiment. In one embodiment, the pharmaceutical composition comprises from about 0% to about 5% w/w of an emulsifier, including each value within the specified range.

Suitable glidant includes, but is not limited to, silicon dioxide and suitable lubricants include, but are not limited to, sodium stearyl fumarate, stearic acid, polyethylene glycol or stearates, such as magnesium stearate, or a mixture or combination thereof. Each possibility represents a separate embodiment. In one embodiment, the pharmaceutical composition comprises from about 0% to about 5% w/w of a glidant or lubricant, including each value within the specified range.

Suitable buffering or pH adjusting agents include, but are not limited to, acidic buffering or pH adjusting agents such as short chain fatty acids, citric acid, acetic acid, hydrochloric acid, sulfuric acid and fumaric acid; and basic buffering or pH adjusting agents such as tris, triethylamine, sodium carbonate, sodium bicarbonate, sodium hydroxide, potassium hydroxide, and magnesium hydroxide, or a mixture or combination thereof. Each possibility represents a separate embodiment. Typically, the buffering or pH adjusting agents are incorporated into the composition in amounts suitable for obtaining a pH in the range of from about 3.5 to about 8.5, including each value within the specified range. In one embodiment, the buffering or pH adjusting agents are incorporated into the composition in amounts suitable for obtaining a pH in the range of from about 4 to about 7, including each value within the specified range. In one embodiment, the pharmaceutical composition comprises from about 0% to about 1% w/w of a buffering or pH adjusting agent, including each value within the specified range.

Suitable tonicity enhancing agents include, but are not limited to, ionic and non-ionic agents. For example, ionic compounds include, but are not limited to, alkali metal or alkaline earth metal halides, such as, for example, $CaCl_2$, KBr, KCl, LiCl, NaI, NaBr or NaCl, and boric acid, or a mixture or combination thereof. Each possibility represents a separate embodiment. Non-ionic tonicity enhancing agents are, for example, urea, glycerol, sorbitol, mannitol, propylene glycol, and dextrose, or a mixture or combination thereof. Each possibility represents a separate embodiment. In one embodiment, the pharmaceutical composition comprises from about 0% to about 5% w/w of a tonicity-enhancing agent, including each value within the specified range.

Suitable wetting agents include, but are not limited to, glycerin, starches, benzododecinium bromide (BOB), and cetrimide (Cet), or a mixture or combination thereof. Each possibility represents a separate embodiment. In one embodiment, the pharmaceutical composition comprises from about 0% to about 5% w/w of a wetting agent, including each value within the specified range.

Suitable thickening agents include, but are not limited to, fatty acids and alcohols such as stearic acid and stearyl alcohol; gums such as xanthan, carrageenan, gelatin, cellulose gum, agarose, karaya, pectin, amylopectin, and locust beans gum; various polymers such as hydroxypropyl methylcellulose (HPMC), hydroxypropyl cellulose (HPC), hydroxymethyl cellulose, hydroxyethyl cellulose, methyl cellulose, calcium carboxymethyl cellulose, polyvinylpyrrolidone (povidone, PVP), polyvinyl alcohol, medium to high molecular weight polyethylene glycols (PEG-3350, PEG-6000, etc.), glucosides, tetrasodium etidronate, polyacrylic acid, polymethacrylic acid, acrylamides copolymer, sodium acrylates copolymer, sodium alginate, calcium alginate, magnesium alginate, alginic acid, hyaluronic acid, polyglucuronic acid (poly-α- and -β-1,4-glucuronic acid), chondroitin sulfate, furcellaran, carboxymethylcellulose, polycarboxylic acids, carbomer, bentonite, chitin, chitosan, carboxymethyl chitin, and cross-linked polyacrylate materials available under the trademark Carbopol®, or a mixture or combination thereof. Each possibility represents a separate embodiment. In one embodiment, the pharmaceutical composition comprises from about 0% to about 30% w/w of a thickening agent, including each value within the specified range.

Suitable suspending agents include, but are not limited to, acacia, alginic acid, bentonite, carbomer, carboxymethylcellulose calcium, carrageenan, colloidal silicon dioxide, dextrin, gelatin, guar gum, hydroxyl ethyl cellulose, hydroxyethyl propylcellulose, hydroxyl propyl cellulose (HPC), hydroxypropyl methylcellulose, methylcellulose, maltodextrin, microcrystalline cellulose (MCC), polydextrose, polyvinyl alcohol, povidone, propylene glycol alginate, sodium alginate, sodium carboxymethylcellulose, starch, tragacanth, and xanthan gum, or a mixture or combination thereof. Each possibility represents a separate embodiment. In one embodiment, the pharmaceutical composition comprises from about 0% to about 30% w/w of a suspending agent, including each value within the specified range.

Suitable preservatives include, but are not limited to, methylparaben, propylparaben, butylparaben, ethylparaben, benzoic acid, potassium sorbate, trisodium EDTA, benzalkonium chloride, tetrasodium EDT, edetate disodium, benzophenone, 2-bromo-2-nitropane-1,3-diol, butylated hydroxytoluene, chlorhexidine digluconate, citric acid, DMDM hydantoin, formaldehyde, methylchloroisothiazolinone, methylisothiazolinone, methyldibromo glutaronitrile, sodium benzoate, phenoxyethanol, ethyl alcohol, benzyl alcohol, chlorobutanol, thimerosal, phenylmercuric nitrate, diazolidinyl urea, imidazolidinyl urea, and quaternium-15, or a mixture or combination thereof. Each possibility represents a separate embodiment. In one embodiment, the pharmaceutical composition comprises from about 0% to about 5% w/w of a preservative, including each value within the specified range.

Suitable antioxidants include, but are not limited to, ascorbic acid, ubiquinone, tocophenyl acetate, ascorbyl palmitate, edetate disodium, and sodium bisulfite, or a mixture or combination thereof. Each possibility represents a separate embodiment. In one embodiment, the pharmaceutical composition comprises from about 0% to about 10% w/w of an antioxidant, including each value within the specified range.

Suitable solvents include, but are not limited to, water, lower alcohols such as ethanol and isopropanol, propylene glycol, ammonium xylenesulfonate, and low molecular weight polyethylene glycols such as, e.g. PEG-300, PEG-1450 etc., or a mixture or combination thereof. Each possibility represents a separate embodiment. Additional solvents include, but are not limited to, oils constituting an oil phase (e.g. in emulsion compositions). Exemplary oil phases include, but are not limited to, Miglyol 810 (medium chain triglyceride), soy lecithin (e.g. phospholipon 90), cholesterol etc., or a mixture or combination thereof. Each possibility represents a separate embodiment. In one embodiment, the pharmaceutical composition comprises from about 0% to about 99.9% w/w of a solvent, including each value within the specified range.

Suitable flavoring agents include, but are not limited to, sweeteners such as sucralose, and synthetic flavor oils and flavoring aromatics, natural oils, extracts from plants, leaves, flowers, and fruits, or a mixture or combinations thereof. Each possibility represents a separate embodiment. Exemplary flavoring agents include cinnamon oils, oil of wintergreen, peppermint oils, clover oil, hay oil, anise oil, eucalyptus, vanilla, citrus oil such as lemon oil, orange oil, grape and grapefruit oil, and fruit essences including apple, peach, pear, strawberry, raspberry, cherry, plum, pineapple, and apricot, or a mixture or combination thereof. Each possibility represents a separate embodiment. In one embodiment, the pharmaceutical composition comprises from about 0% to about 5% w/w of a flavoring agent, including each value within the specified range.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, disodium dityrylbiphenyl, mica, dentifrices, talc, titanium dioxide, aluminum powder, bronze powder, copper powder, and zinc oxide, or a mixture or combination thereof. Each possibility represents a separate embodiment. In one embodiment, the pharmaceutical composition comprises from about 0% to about 5% w/w of a colorant, including each value within the specified range.

According to certain aspects and embodiments where ocular administration is desired, the pharmaceutically acceptable excipient is preferably at least one of a buffering or a pH adjusting agent, a preservative, an antioxidant, a filler, a surfactant, a wetting agent, a thickening agent, a suspending agent, a tonicity enhancing agent, a solvent, and a mixture or combination thereof as defined hereinabove. Each possibility represents a separate embodiment. Additionally, the pharmaceutical composition for ocular administration may further comprise an osmotic agent, a chelating agent, or a mixture or combination thereof. Each possibility represents a separate embodiment.

Suitable osmotic agents include, but are not limited to, mannitol, glycerol, sorbitol, and xylitol, or a mixture or combination thereof, with each possibility representing a separate embodiment. In one embodiment, the pharmaceutical composition comprises from about 0% to about 5% w/w of an osmotic agent, including each value within the specified range.

Suitable chelating agents include, but are not limited to, disodium edetate, deferoxamine mesylate (desferrioxamine), 2,3-dimercaprol, meso-2,3-dimercaptosuccinic acid (DMSA) and its ester analogues, deferiprone, and nitrilotriacetic acid (NTA), or a mixture or combination thereof. Each possibility represents a separate embodiment. In one embodiment, the pharmaceutical composition comprises from about 0% to about 5% w/w of a chelating agent, including each value within the specified range.

The pharmaceutical compositions of the present invention may be manufactured by processes well known in the art, e.g., by means of conventional mixing, dissolving, suspending, solubilizing, complexing, granulating, levigating, emulsifying, encapsulating, entrapping, spray-drying, and lyophilizing processes, or a combination thereof. They may be formulated in a conventional manner using one or more pharmaceutically acceptable excipients as described above, which facilitate processing of the peptides and peptide derivatives and salts into preparations which can be used as medicaments. Proper formulation is dependent upon the route of administration chosen. In particular, the pharmaceutical compositions of the present invention are formulated for topical (e.g. ocular), oral, transdermal, intra-arterial, intranasal, intraperitoneal, intramuscular, subcutaneous, or intravenous administration. Each possibility represents a separate embodiment.

The pharmaceutical compositions of the present invention may be formulated in a form selected from the group consisting of solution, suspension, dispersion, emulsion, oil, ointment, gel, cream, lotion, tablet, pill, capsule (e.g. soft or hard gelatin capsule), pellets, granules, powder, a wafer, coated or uncoated beads, lozenge, sachet, cachet, elixir, an osmotic pump, a depot system, an iontophoretic system, a patch, syrup, aerosol, and suppository. Each possibility represents a separate embodiment. Alternative forms in which the pharmaceutical compositions of the present invention may be formulated include forms that are designed for reconstitution with a suitable vehicle prior to use. For ocular, topical administration, the compositions are preferably formulated as solution, suspension, dispersion, emulsion, oil, ointment, gel, cream, or lotion. Each possibility represents a separate embodiment. In one embodiment, the pharmaceutical composition is in the form of a liposomal suspension.

The pharmaceutical compositions of the present invention may be formulated as single-phase aqueous emulsion or multiple emulsions. According to some embodiments, the composition is formulated as an emulsion. These emulsions may be oil-in-water (o/w) emulsions, water-in-oil (w/o) emulsions, or multiple emulsions such as oil-in-water-in-oil (o/w/o) or water-in-oil-in-water (w/o/w) emulsions. It is understood that the oil phase can comprise silicone oils, non-silicone organic oils, or mixtures thereof. The compositions can comprise two immiscible phases that are reconstituted prior to use. Each possibility represents a separate embodiment of the present invention.

The compositions of the present invention are useful in treating, preventing, minimizing, diminishing or reversing a disease associated with ROS-related oxidative stress. As used herein, the term "oxidative stress" refers to disturbance in the pro-oxidant/antioxidant balance in favor of the pro-oxidant, leading to potential damage. The term "reactive oxygen species" (ROS) as used herein relates to one or a combination of the following: i) highly reactive ions in which the charge is located on the oxygen atom; ii) free radicals, namely chemical species with a molecular orbital containing a single unpaired electron, wherein the molecular orbital containing the single unpaired electron is located on an oxygen atom; iii) diradicals, namely a molecular species with two electrons occupying two degenerate molecular orbitals of the same energy; iv) hydrogen peroxide ($H_2O_2$); v) organic hydroperoxides, R—O—O—H, wherein R is an organic group; vi) organic peroxides, R—O—O—R', wherein R and R' are identical or non-identical organic groups; and vii) ozone. Non-limiting examples of reactive oxygen species are superoxide anion, hydroperoxide anion, hydroxyl radical, singlet oxygen, hypochloride anion, tert-butyl hydroperoxide (($CH_3$)$_3$C—O—O—H) and the like.

In some aspects and embodiments, the present invention provides the treatment, prevention, minimization, diminishment or reversal of a degenerative, age-related or trauma-induced disease or disorder. As used herein and in the appended claims, the terms "treating, preventing, minimizing, diminishing or reversing" refer to abrogating, inhibiting, slowing or reversing the progression of a disease, ameliorating clinical symptoms of a disease or preventing the appearance of clinical symptoms of a disease. The term "preventing" is defined herein as barring a subject from acquiring a disorder or disease. In accordance with these embodiments, the peptides and compositions of the present invention are contemplated to afford neuroprotection as well as the prevention of apoptosis of cells and the protection and facilitation of healing of corneal epithelial tissue. The term "administering" as used herein refers to bringing into contact with a peptide of the present invention or composition comprising same thus providing the aforementioned therapeutic benefits to a subject, preferably a human subject.

According to various aspects and embodiments, the peptide of the present invention or composition comprising same is useful in treating, preventing, minimizing, diminishing or reversing a neurodegenerative disease including, but not limited to, Alzheimer's disease, Parkinson's disease, Huntington's disease, and Amyotrophic Lateral Sclerosis (ALS). Each possibility represents a separate embodiment. Alzheimer's disease refers to all types and stages of the disease including early stages which are characterized by memory deficits as well as later stages that are characterized by symptoms such as impaired judgment, disorientation, confusion, behavior changes, speech impairment, and motor deficits. Histologically, Alzheimer's disease is characterized by beta-amyloid plaques and tangles of protein tau. Parkinson's disease is a disease that belongs to a group of chronic and progressive conditions called movement disorders and is characterized by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Secondary symptoms may include high level cognitive dysfunction and subtle language problems. Huntington's disease refers to a neurodegenerative disease caused by the expansion of a polyglutamine tract at the N-terminus of the protein huntingtin (expressed by the HTT gene). The disease is characterized by progressive neuronal death in different brain areas, including toxicity in medium-sized spiny neurons of the striatum that determines the appearance of the classic motor incoordination and movements such as "Chorea". Amyotrophic lateral sclerosis refers to a progressive, fatal, neurodegenerative disease characterized by a degeneration of motor neurons, the nerve cells in the central nervous system that control voluntary muscle movement. ALS is also characterized by neuronal degeneration in the entorhinal cortex and hippocampus, memory deficits, and neuronal hyperexcitability in different brain areas such as the cortex. Additional diseases within the scope of the present invention include, but are not limited to, atherosclerosis, and chronic obstructive pulmonary disease (COPD). Each possibility represents a separate embodiment.

Within the scope of the present invention is the treatment, prevention, minimization, diminishment or reversal of degenerative eye disease or disorder. In various embodiments, the degenerative or age-related eye disease or disorder is age-related macular degeneration (AMD). AMD is typically characterized by two stages termed the "dry" form and the "wet" form. The dry form represents an initial stage of the disease that progresses to the wet form characterized by abnormal growth of blood vessels behind the affected retina. The progression of AMD is being associated with the consequences of oxidative stress species (Byeon et al. Invest. Ophthal. & Vis. Sci., 5, 1190-1197, 2010). In other embodiments, the degenerative or age-related eye disease or disorder is glaucoma. Glaucoma belongs to a group of optic nerve neuropathies characterized by apoptosis of Retinal Ganglion Cells (RGC). In some embodiments, the glaucoma is selected from the group consisting of primary open-angle glaucoma, primary angle-closure glaucoma, secondary open-angle glaucoma, secondary angle-closure glaucoma, pigmentary glaucoma, neovascular glaucoma, pseudophakic glaucoma, malignant glaucoma, uveitic glaucoma, glaucoma due to peripheral anterior synechia, and combinations thereof. Each possibility represents a separate embodiment. In additional embodiments, the degenerative or age-related eye disease or disorder is cataract. Cataract originates from opacification of the eye lens and the loss of lens's transparency typically attributed to modifications in lens' proteins. Cataract has also been suggested as associated with ROS-related oxidative stress. In further embodiments, the trauma-induced eye disease or disorder is trauma which is induced following cataract surgery. In one embodiment, the trauma-induced eye disease or disorder is other than chemically induced corneal injury. In another embodiment, the degenerative or age-related eye disease or disorder is Fuchs' Corneal Dystrophy (FCD). FCD is typically associated with deposits (guttae) that develop under the corneal endothelium. These deposits were suggested to be associated with oxidative stress that leads to apoptosis of corneal endothelial cells. In additional embodiments, the trauma-induced eye disease or disorder is corneal erosion. Corneal erosion results from an injury to the corneal surface or corneal trauma. It is to be understood that the treatment of corneal erosion as used herein does not include the treatment of pain as a symptom of corneal erosion.

As used herein and in the appended claims, the terms "treating, preventing, minimizing, diminishing or reversing" refer to, in some embodiments, improvement in at least one parameter of vision, which typically declines with age. The improvement may be in a parameter that already deteriorated due to old age. In various embodiments, the terms "treating, preventing, minimizing, diminishing or reversing" refer to the prophylaxis of age-related deterioration of at least one parameter of vision. The prophylactic effect may be expressed by prevention of the deterioration or decrease in the level of deterioration as compared to untreated control; decrease in the rate of deterioration; or postponement in the age of the onset of deterioration as compared to untreated control. The term "at least one parameter of the eye that deteriorates with age" refers to any physiological (electrical, metabolic), structural (histological), biochemical or functional parameter, or combination of parameters that are known in the field to decrease with old age. Preferably, these are parameters relating to the physiological functions of the retina. These parameters include ERG which measures the electrophysiological function of the retina; behavioral tests including perimetry, contrast sensitivity, motion perception, visual acuity, binocular vision, visual threshold and color perception; the number of cells in the outer, mid or inner retina and RPE; retinal layer thickness; and changes in genetic, molecular and cellular processes controlling apoptosis in the retina. Additional parameters of the visual system relating to optic nerve fiber include the number and size of optic nerve axons; thickness of the optic nerve and its meningeal sheaths; number of glial cells and the related GFAP-immunoreactive area in the optic nerve; changes in optic nerve gene expression controlling the above processes; and changes in the optic nerve responses controlling the above processes. As contemplated by the present invention, treatment comprises the direct action of the peptides or salts of the invention on the lens as well as the indirect attenuation of the formation of ROS and increase in viability of corneal cells being subjected to oxidative stress conditions. It is to be understood that treatment, prevention, minimization, diminishment, or reversal of degenerative, age-related or trauma-induced eye disease or disorder according to the present invention does not include the treatment of pain or inflammation which may accompany any one of the aforementioned disorders.

Pharmaceutical compositions suitable for use in the context of the present invention include compositions wherein the peptide of the invention is contained in an amount effective to achieve the intended purpose. More specifically, an effective amount means an amount of the peptide that is effective to treat, prevent, minimize, diminish or reverse any one of the aforementioned diseases or disorders.

Determination of an effective amount is well within the capability of those skilled in the art, especially in light of the detailed disclosure provided herein. For any preparation used in the methods of the invention, the effective amount can be estimated initially from in vitro and cell culture assays as well as in-vivo in various animal models known to those of skill in the art. For example, a certain dose can be formulated in an animal model to achieve a desired concentration or titer. Such information can be used to more accurately determine useful doses in humans. The dosage may vary depending upon the dosage form employed and the route of administration utilized. The exact formulation, route of administration and dosage can be chosen in view of the subject's condition. Although the compositions of the present invention may be administered at a single dose, multiple administrations at certain intervals are contemplated within the scope of the present invention. These may be adjusted according to individual characteristics and route of administration depending on the severity and responsiveness of the condition being treated. The duration of treatment may last from several days to several weeks, months or years as desired.

In certain embodiments, the dosage of the peptide or salt thereof will be within the range of about 0.001-1000 mg/kg of body weight, for example about 0.01 mg/kg to about 100 mg/kg, about 0.1 mg/kg to about 100 mg/kg, or about 1 mg/kg to about 100 mg/kg etc., including each value within the specified ranges. Exemplary non-limiting amounts of the peptide of the present invention or salt thereof include about 0.001 mg/kg, about 0.005 mg/kg, about 0.01 mg/kg, about 0.05 mg/kg, about 0.1 mg/kg, about 0.5 mg/kg, about 1 mg/kg, about 5 mg/kg, about 10 mg/kg, about 50 mg/kg, about 100 mg/kg, about 500 mg/kg, and about 1000 mg/kg. Each possibility represents a separate embodiment. Alternatively, the amount administered can be measured and expressed as molarity of the administered compound. By way of illustration and not limitation, the peptide of the present invention or salt thereof can be administered in a range of about 0.1 to about 10 mM, including each value within the specified range e.g., about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 mM. Each possibility represents a separate embodiment. Alternatively, the amount administered can be measured and expressed as mg/ml, µg/ml, or ng/ml.

As used herein the term "about" refers to ±10%.

The terms "comprise", "comprising", "include", "including", "having" and their conjugates mean "including, but not limited to".

As used herein, the singular form "a", "an" and "the" include plural references unless the context clearly dictates otherwise. For example, the term "a peptide" or "an excipient" may include a plurality of peptides and excipients, including mixtures thereof.

Throughout this application, various embodiments of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as $C_4$-$C_{30}$ alkyl should be considered to have specifically disclosed subranges such as, but not limited to $C_4$-$C_{25}$ alkyl, $C_4$-$C_{20}$ alkyl, $C_4$-$C_{15}$ alkyl, $C_4$-$C_{10}$ alkyl, $C_6$-$C_{10}$ alkyl, etc., as well as individual numbers within that range, for example, $C_5$ alkyl, $C_7$ alkyl, $C_8$ alkyl etc. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Example 1. Formulations

Exemplary ocular formulations of the present invention are outlined in Tables 1-5 below:

TABLE 1

ZEP3/ZEP3Na Ocular solution

| Ingredient | Material Class | w/w % |
|---|---|---|
| ZEP3/ZEP3Na | Active ingredient | 1 |
| Tyloxapol | Surfactant | 0.3 |
| Povidone C-30 | Suspending agent | 0.6 |
| Benzalkonium chloride | Preservative | 0.01 |
| Edetate disodium | Antioxidant | 0.01 |
| Purified Water | Solvent | q.s. to 100 |

TABLE 2

ZEP3/ZEP3Na Ocular gel

| Ingredient | Material Class | w/w % |
|---|---|---|
| ZEP3/ZEP3Na | Active ingredient | 1 |
| Polysorbate (Tween 80) | Surfactant | 0.1 |
| Carbopol ® | Thickening agent | 0.5 |
| Triethylamine | Buffering agent | 0.01 |
| Benzalkonium chloride | Preservative | 0.01 |
| Edetate disodium | Antioxidant | 0.01 |
| Purified Water | Solvent | q.s. to 100 |

TABLE 3

ZEP3/ZEP3Na Cyclodextrin-based solution

| Ingredient | Material Class | w/w % |
|---|---|---|
| ZEP3/ZEP3Na | Active ingredient | 1 |
| Cyclodextrin (β-random methylated; β-hydroxypropyl; sulfobutylether-hydroxypropyl) | Filler | 20 |

TABLE 3-continued

ZEP3/ZEP3Na Cyclodextrin-based solution

| Ingredient | Material Class | w/w % |
|---|---|---|
| Benzalkonium chloride | Preservative | 0.01 |
| Edetate disodium | Antioxidant | 0.01 |
| Purified Water | Solvent | q.s. to 100 |

TABLE 4

ZEP3/ZEP3Na Ophthalmic emulsion

| Ingredient | Material Class | w/w % |
|---|---|---|
| ZEP3/ZEP3Na | Active ingredient | 1 |
| Miglyol 810 (medium chain triglyceride) | Oil phase | 5 |
| PEG-tocopherol succinate (TPGS) | Surfactant | 0.5 |
| Benzalkonium chloride | Preservative | 0.01 |
| Edetate disodium | Antioxidant | 0.01 |
| Purified Water | Solvent | q.s. to 100 |

TABLE 5

ZEP3/ZEP3Na Liposomal suspension

| Ingredient | Material Class | w/w % |
|---|---|---|
| ZEP3/ZEP3Na | Active ingredient | 1 |
| Soy lecithin (Phospholipon 90) | Oil phase | 6 |
| Cholesterol | Oil phase | 2 |
| Benzalkonium chloride | Preservative | 0.01 |
| Edetate disodium | Antioxidant | 0.01 |
| Purified Water | Solvent | q.s. to 100 |

Example 2. Glaucoma

In order to evaluate the effect of the peptide of the present invention or salt thereof on glaucoma, a rat model as described in Morrison et al. (Exp. Eye Res., 141, 23-32, 2015) is used. The study involves injection of hypertonic saline to elevate the intraocular pressure and elicit a pattern of optic nerve injuries. Rats that are treated with eye drops containing 1% w/w of peptide or salt thereof (e.g. ZEP3Na, ZEP4Na) are compared to rats that are treated with vehicle.

Another model for evaluating the effect of the peptide of the present invention or salt thereof on glaucoma is the rat optic nerve crush model described in Lin et al. (https://doi.org/10.1371/journal.pone.0178584). This model uses a traumatic optic neuropathy leading to degeneration of the damaged axonal optic nerves. The effect of the peptide of the present invention or salt thereof (e.g. ZEP3Na, ZEP4Na) is assessed by measuring the restoration of the optic nerve conductance and by observing the cell death among the retina.

Example 3. Cataract

In order to evaluate the effect of the peptide of the present invention or salt thereof on cataract, a model as described in Shearer et al. (Mol. Vis. 3, 8-16, 1997) or in Nakazawa et al. (Mol. Vis. 21, 804-810, 2015) is used. In particular, cataract is induced by injection of sodium selenite. The degree of the formed lens serves as a measurement for the efficacy of the prevention of cataract formation by the peptide of the present invention or salt thereof (e.g. ZEP3Na, ZEP4Na) vs. vehicle.

Example 4. Ocular Injury

In order to evaluate the effect of the peptide of the present invention or salt thereof in preventing epithelial apoptotic damage, an ocular injury is induced by transient formaldehyde exposure in a rabbit eye model as described in Lai et al. (https://doi.org/10.1371/journal.pone.0066649). The efficacy of the peptide of the present invention or salt thereof (e.g. ZEP3Na, ZEP4Na) is evaluated by assessing the decrease in the parameters of the damage produced by a defined exposure to a specified concentration of formaldehyde vs. vehicle.

Example 5. Fuchs Endothelial Corneal Dystrophy (FECD)

In order to evaluate the effect of the peptide of the present invention or salt thereof on FECD, the ocular oxidative stress induced senescence is assessed. Human corneal cells are incubated with the peptide of the present invention or salt thereof (e.g. ZEP3Na, ZEP4Na) vs. vehicle.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

The invention claimed is:

1. A method of treating a degenerative, age-related, or trauma-induced disease or disorder in a subject in need thereof, the method comprising administering to the subject a pharmaceutical composition comprising as an active ingredient a peptide of Formula I: pGlu-$X_1$-$X_2$-$X_3$-OH, wherein:

$X_1$ is selected from the group consisting of Asn and Thr;

$X_2$ is selected from the group consisting of Trp, Phe and Tyr; and $X_3$ is selected from the group consisting of Lys, Lys attached through its amino side chain to a $C_4$-$C_{30}$ alkyl group, and Thr; or a salt or derivative thereof, and a pharmaceutically acceptable carrier, wherein the degenerative, age-related, or trauma-induced disease or disorder is a neurodegenerative disease or disorder selected from the group consisting of Alzheimer's disease, Parkinson's disease, Huntington's disease, and Amyotrophic Lateral Sclerosis (ALS) or a degenerative, age-related, or trauma-induced eye disease or disorder selected from the group consisting of glaucoma, Fuchs' corneal dystrophy, cataract or trauma induced following cataract surgery, corneal erosion, and age-related macular degeneration.

2. The method of claim 1, wherein the peptide of Formula I or a salt or derivative thereof has an amino acid sequence of pGlu-Asn-Trp-Lys(Octanoyl)-OH as set forth in SEQ ID NO: 1 or a salt thereof.

3. The method of claim 2, wherein the peptide is the sodium salt of the peptide having an amino acid sequence as set forth in SEQ ID NO: 1.

4. The method of claim 1, wherein the peptide of Formula I or a salt or derivative thereof has an amino acid sequence of pGlu-Asn-Trp-Thr-OH as set forth in SEQ ID NO: 2 or a salt thereof.

5. The method of claim 4, wherein the peptide is the sodium salt of the peptide having an amino acid sequence as set forth in SEQ ID NO: 2.

6. The method of claim 1, wherein the composition comprises from about 0.1% to about 5% w/w of the peptide of Formula I or a salt or derivative thereof.

7. The method of claim 1, wherein the administration route is selected from the group consisting of topical, oral, transdermal, intra-arterial, intranasal, intraperitoneal, intramuscular, subcutaneous, and intravenous.

8. The method of claim 7, wherein the pharmaceutical composition is in a form selected from the group consisting of solution, suspension, dispersion, emulsion, oil, ointment, gel, cream, lotion, tablet, pill, capsule, pellets, granules, powder, a wafer, coated or uncoated beads, lozenge, sachet, cachet, elixir, an osmotic pump, a depot system, an iontophoretic system, a patch, syrup, aerosol, and suppository.

9. The method of claim 1, wherein the pharmaceutically acceptable carrier comprises at least one of a binder, a filler, a diluent, a surfactant or emulsifier, a glidant or lubricant, a buffering or pH adjusting agent, a tonicity enhancing agent, a wetting agent, a thickening agent, a suspending agent, a preservative, an antioxidant, a solvent, a flavoring agent, a colorant, and a mixture or combination thereof.

10. The method of claim 1, wherein the degenerative disease or disorder is a neurodegenerative disease or disorder selected from the group consisting of Alzheimer's disease, Parkinson's disease, Huntington's disease, and Amyotrophic Lateral Sclerosis (ALS).

11. A method of treating a degenerative, age-related, or trauma-induced eye disease or disorder in a subject in need thereof, the method comprising administering to the subject a pharmaceutical composition comprising as an active ingredient a peptide of Formula I: pGlu-$X_1$-$X_2$-$X_3$-OH, wherein:

$X_1$ is selected from the group consisting of Asn and Thr;

$X_2$ is selected from the group consisting of Trp, Phe and Tyr; and $X_3$ is selected from the group consisting of Lys, Lys attached through its amino side chain to a $C_4$-$C_{30}$ alkyl group, and Thr; or a salt or derivative thereof, and a pharmaceutically acceptable carrier.

12. The method of claim 11, wherein the degenerative, age-related, or trauma-induced eye disease or disorder is selected from the group consisting of glaucoma, Fuchs' corneal dystrophy, cataract or trauma induced following cataract surgery, corneal erosion, and age-related macular degeneration.

13. The method of claim 11, wherein the administration route is ocular.

14. The method of claim 13, wherein the pharmaceutical composition is in a form selected from the group consisting of solution, suspension, dispersion, emulsion, oil, ointment, gel, cream, and lotion.

15. A method of treating a disease associated with ROS-related oxidative stress in a subject in need thereof, the method comprising administering to the subject a pharmaceutical composition comprising as an active ingredient a peptide of Formula I: pGlu-$X_1$-$X_2$-$X_3$-OH, wherein:

$X_1$ is selected from the group consisting of Asn and Thr;

$X_2$ is selected from the group consisting of Trp, Phe and Tyr; and $X_3$ is selected from the group consisting of Lys, Lys attached through its amino side chain to a $C_4$-$C_{30}$ alkyl group, and Thr; or a salt or derivative thereof, and a pharmaceutically acceptable carrier, wherein the disease associated with ROS-related oxidative stress is a neurodegenerative disease or disorder selected from the group consisting of Alzheimer's disease, Parkinson's disease, Huntington's disease, and Amyotrophic Lateral Sclerosis (ALS); or a disease selected from the group consisting of glaucoma, Fuchs' corneal dystrophy, cataract or trauma induced following cataract surgery, corneal erosion, and age-related macular degeneration.

16. The method of claim 11, wherein the peptide of Formula I is selected from the group consisting of pGlu-Asn-Trp-Lys(Octanoyl)-OH (SEQ ID NO: 1), pGlu-Asn-Trp-Thr-OH (SEQ ID NO: 2), and salts thereof.

17. The method of claim 12, wherein the peptide of Formula I is selected from the group consisting of pGlu-Asn-Trp-Lys(Octanoyl)-OH (SEQ ID NO: 1), pGlu-Asn-Trp-Thr-OH (SEQ ID NO: 2), and salts thereof.

18. The method of claim 15, wherein the disease associated with ROS-related oxidative stress is a neurodegenerative disease or disorder selected from the group consisting of Alzheimer's disease, Parkinson's disease, Huntington's disease, and Amyotrophic Lateral Sclerosis (ALS).

19. The method of claim 15, wherein the disease associated with ROS-related oxidative stress is selected from the group consisting of glaucoma, Fuchs' corneal dystrophy, cataract or trauma induced following cataract surgery, corneal erosion, and age-related macular degeneration.

20. The method of claim 15, wherein the peptide of Formula I is selected from the group consisting of pGlu-Asn-Trp-Lys(Octanoyl)-OH (SEQ ID NO: 1), pGlu-Asn-Trp-Thr-OH (SEQ ID NO: 2), and salts thereof.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: pyroglutamic acid (pGlu)
<220> FEATURE:
<221> NAME/KEY: MOD_RES
<222> LOCATION: (4)..(4)
<223> OTHER INFORMATION: C8 alkyl attached to the epsilon amine of the
      Lysine side chain to form Lys(Octanoyl)

<400> SEQUENCE: 1

Glu Asn Trp Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: pyroglutamic acid (pGlu)

<400> SEQUENCE: 2

Glu Asn Trp Thr
1
```